United States Patent [19]

Chen et al.

[11] Patent Number: 5,360,927
[45] Date of Patent: Nov. 1, 1994

[54] PROCESS FOR THE PREPARATION OF MONOHYDRATED SODIUM PHENYLPYRUVATE

[75] Inventors: Jin-Tann Chen, Taipei; Same-Ting Chen, Yuanlin; Hsin Tsai, Taipei, all of

[73] Assignee: Development Center for Biotechnology, Taipei,

[21] Appl. No.: 185,714

[22] Filed: Jan. 24, 1994

[51] Int. Cl.$^5$ ............................................. C07C 59/74
[52] U.S. Cl. .................................................. 562/459
[58] Field of Search ...................................... 562/459

[56] References Cited

U.S. PATENT DOCUMENTS

| | | | |
|---|---|---|---|
| 4,152,352 | 5/1979 | Perron | 562/406 |
| 4,351,952 | 9/1982 | Foa | 562/406 |
| 4,492,798 | 1/1985 | Lee | 562/406 |
| 4,518,800 | 5/1985 | Schouteeten | 562/459 |
| 4,689,431 | 8/1987 | Tanaka | 562/406 |

FOREIGN PATENT DOCUMENTS 1043136 1/1986 Japan .

OTHER PUBLICATIONS

Herbst, R. M. et al. Org. Syn. Coll. 3 1943, pp. 519–520.

*Primary Examiner*—Paul J. Killos
*Attorney, Agent, or Firm*—Ladas & Parry

[57] ABSTRACT

A process for the preparation of monohydrated sodium phenylpyruvate comprises reacting benzaldehyde with the stoichiometric quantity of hydantoin in the aqueous medium in the presence of a catalytic quantity of a primary or secondary amine at high temperature, treating the reaction mixture with an excess of sodium hydroxide at high temperature, adding sodium chloride to the sodium hydroxide-treated solution, acidifying the so obtained solution with concentrated hydrochloric acid, and washing the formed precipitate with methanol.

6 Claims, No Drawings

PROCESS FOR THE PREPARATION OF MONOHYDRATED SODIUM PHENYLPYRUVATE

BACKGROUND OF THE INVENTION

1. Field of the Invention

The present invention relates to a process for preparing monohydrated sodium phenylpyruvate.

2. Description of the Prior Art

Phenylpyruvic acid or the salt thereof is a useful raw material for preparing phenylalanine. Phenylpyruvic acid can be prepared by acid hydrolysis of α-acetamidocinnamic acid (Herbst, R. M. and Shemin, D. (1943) Org. Syn. Coil. 3, 519) or by biscarbonylation of benzylchloride (General Director of Agency of Industrial Science and Technology and Nissan Chemical Industries, Ltd., Japan (1987) U.S. Pat. No. 4,689,431; Ethyl Corporation (1985) U.S. Pat. No. 4,492,798; Montedison S.p.A. (1982) U.S. Pat. No. 4,351,952; Rhone-Poulenc Industries (1979) U.S. Pat. No. 4,152,352). However, phenylpyruvic acid is not a stable compound at room temperature. Instability causes storage and transportation problems.

U.S. Pat. No. 4,518,800 issued to Schouteeten et al. on May 21, 1985 discloses that monohydrated sodium phenylpyruvate, which is a stable compound, can be prepared by reacting benzaldehyde with the stoichiometric quantity of hydantoin in an aqueous medium in the presence of a catalytic quantity of ethanolamine at high temperature, treating the reaction mixture with an excess of sodium hydroxide, acidifying the obtained solution to pH 9 with concentrated hydrochloric acid, and washing the formed precipitate with iced water. However, there are two main disadvantages in the above-mentioned process for the preparation of monohydrated sodium phenylpyruvate. First, much excess sodium hydroxide is used. This subsequently leads to an increase in the amount of hydrochloric acid used. Second, washing monohydrated sodium phenylpyruvate with iced water substantially reduces the yield, since monohydrated sodium phenylpyruvate is soluble in water. To check the yield of monohydrated sodium phenylpyruvate, the inventors followed the process as described in U.S. Pat. No. 4,518,800, and found that the first isolation yield of monohydrated sodium phenylpyruvate was about 52% of the theoretical value instead of 75% and the overall yield was about 84% instead of 99%, based on HPLC analysis. The low yield in the first isolation is due to the washing of the product with iced water as monohydrated sodium phenylpyruvate is soluble in iced water. The overestimated overall yield (99%) in U.S. Pat. No. 4,518,800 is a result of the presence of large portion of sodium chloride in the second isolation products. The present invention provides a more economic process for the preparation of monohydrated sodium phenylpyruvate in high yield.

SUMMARY OF THE INVENTION

It is therefore an object of the present invention to provide a process for the preparation of monohydrated sodium phenylpyruvate in high yield.

Another object of the present invention is to provide a more economic process for the preparation of monohydrated sodium phenylpyruvate.

These objects, advantages and features of the present invention will be more fully understood and appreciated by reference to the written specification.

DETAILED DESCRIPTION OF THE INVENTION

The present invention relates to a process for the preparation of monohydrated sodium phenylpyruvate. The process in accordance with the invention comprises the steps of:

(a) reacting benzaldehyde with the stoichiometric quantity of hydantoin in an aqueous medium in the presence of a catalytic quantity of a primary or secondary amine at reflux temperature;

(b) treating the reaction mixture with an excess of sodium hydroxide at reflux temperature;

(c) adding sodium chloride to the sodium hydroxide-treated solution;

(d) acidifying the solution obtained in step (c) with concentrated hydrochloric acid; and (e) washing the precipitate formed in step (d) with a primary alcohol.

The present invention discloses that primary or secondary amines can be used in catalyzing the reaction of benzaldehyde with the stoichiometric quantity of hydantoin to form 5-benzylidene hydantoin in an aqueous medium. 5-Benzylidene hydantoin, an intermediate for the preparation of phenylpyruvate, is prepared by reacting benzaldehyde with the stoichiometric quantity of hydantoin in an aqueous medium in the presence of a catalytic quantity of a primary or secondary amine under reflux for 4 hours or longer, depending upon the types of amines used. The preferred amines are primary or secondary amines which have a boiling point higher than 100° C. Particularly the preferred amines are 1-amino-2-propanol, cyclohexylamine and diethanolamine. When 1-amino-2-propanol, a primary amine, is used as a catalyst and the molar ratio of benzaldehyde to hydantoin to the catalyst is 1:1:0.1, the reaction is completed in 4 hours. When diethanolamine, a secondary amine, is used as a catalyst and the molar ratio of benzaldehyde to hydantoin to diethanolamine is 1:1:0.5, the reaction is almost completed in 8 hours. When cyclohexylamine, a cyclic primary amine, is used as a catalyst and the molar ratio of benzaldehyde to hydantoin to cyclohexylamine is 1:1:0.2, the reaction is completed in 14 hours. Accordingly, in addition to ethanolamine, other amines are useful as catalysts to catalyze the formation of 5-benzylidene hydantoin.

According to the present invention, 5-benzylidene hydantoin can be completely hydrolyzed by a comparatively low amount of sodium hydroxide. However, when the ratio of sodium hydroxide to hydantoin is less than 2:1, the hydrolysis reaction is unable to reach completion. In order to increase the concentration of sodium hydroxide, the volume of water is proportionally reduced. The preferred ratio of sodium hydroxide to hydantoin ranges from 2 to 5. Particularly the preferred ratio of sodium hydroxide to hydantoin is 3. When 1-amino-2-propanol is used as a catalyst and the molar ratios of sodium hydroxide to hydantoin are individually 2:1, 2.5:1, 3:1, 3.5:1 and 5:1, the reactions are completed in 110, 100, 85, 70 and 50 minutes respectively. To reach a compromise between the reaction time and the amount of sodium hydroxide, the molar ratio of sodium hydroxide to hydantoin is preferably 3:1. Lesser amount of sodium hydroxide gives two advantages in the invention. That is, less quantity of concentrated

3 hydrochloric acid is needed to obtain monohydrated sodium phenylpyruvate, and the unit reactor produces more products, since the volume of the reaction is reduced. These two advantages result in a decrease in production cost.

The present invention also discloses that the addition of sodium chloride to the sodium hydroxide-treated solution increases the precipitation of monohydrated sodium phenylpyruvate upon acidification. When the concentration of sodium chloride is maintained around 5.5M, almost all sodium phenylpyruvate precipitates as monohydrated sodium phenylpyruvate at pH 8.5—only about 2.3% left in the mother liquor.

In the present invention, washing the collected monohydrated sodium phenylpyruvate precipitate with methanol not only removes the yellow impurity but also facilitates the drying of the products. The other main reason for selecting methanol as a washing agent is that monohydrated sodium phenylpyruvate is sparingly soluble in methanol. When water is used as a washing agent, it does not have the aforementioned advantages.

The following examples will serve to illustrate the present invention. These examples are not to be construed as limiting the scope of the present invention.

EXAMPLES

EXAMPLE 1

In a 2-L three-necked, round-bottomed flask, fitted with a mechanical stirrer and a reflux condenser, were placed 120 g (1.2 moles) of hydantoin, 127 g (1.2 moles) of benzaldehyde and 9.0 g (0.12 mole) of 1-amino-2-propanol in 300 ml of water. The flask was then placed in an oil bath which had been heated to a temperature of 130°–135° C. After the mixture was refluxed for 4 hours, 1.20 kg of 20% (6 moles) hot sodium hydroxide solution was added. The mixture was continued to reflux for 50 minutes.

The so obtained solution was transferred to a 3-L beaker, cooled in an ice bath, and brought to pH 8.5 by the addition of about 400 ml of concentrated hydrochloric acid (37%). The desired product, monohydrated sodium phenylpyruvate, precipitated slowly. The mixture was let to stand at room temperature for 16 hours.

The precipitate was filtered on a Büchner funnel, washed with 1.2 liters of methanol, and transferred to a 3-L beaker. It was then stirred with 960 ml of methanol, filtered again on a Büchner funnel, and washed with 1.8 liters of methanol. After drying in a vacuum oven at 25° C. to a constant weight, 173 g (71% of the theoretical value) of monohydrated sodium phenylpyruvate was obtained in the form of a white solid. The purity was over 98%.

EXAMPLE 2

In a 2-L three-necked, round-bottomed flask, fitted with a mechanical stirrer and a reflux condenser, were placed 120 g (1.2 moles) of hydantoin, 127 g (1.2 moles) of benzaldehyde and 9.0 g (0.12 mole) of 1-amino-2-propanol in 300 ml of water. The flask was then placed in an oil bath which had been heated to a temperature of 130°–135° C. After the mixture was refluxed for 4 hours, 1.13 kg of 15% (4.2 moles) sodium hydroxide was added. The mixture was continued to reflux for 70 minutes. HPLC analysis showed that 5-benzylidene hydantoin formed by condensing benzaldehyde and hydantoin was almost converted into phenylpyruvate and other minor side products.

EXAMPLE 3

The procedure of Example 2 was repeated except that 720 g of 20% (3.6 moles) sodium hydroxide was added and the mixture was continued to reflux for 85 minutes. HPLC analysis showed that 5-benzylidene hydantoin was completely converted into phenylpyruvate and other minor side products.

EXAMPLE 4

The procedure of Example 2 was repeated except that 600 g of 20% (3 moles) sodium hydroxide solution was added and the mixture was continued to reflux for 100 minutes. HPLC analysis showed that 5-benzylidene hydantoin was completely converted into phenylpyruvate and other minor side products.

EXAMPLE 5

The procedure of Example 2 was repeated except that 480 g of 20% (2.4 moles) sodium hydroxide solution was added and the mixture was continued to reflux for 110 minutes. HPLC analysis showed that 5-benzylidene hydantoin was almost completely converted into phenylpyruvate and other minor side products.

EXAMPLE 6

The procedure of Example 2 was repeated except that 300 g of 20% (1.5 moles) sodium hydroxide solution was added and the mixture was continued to reflux for 50 minutes. HPLC analysis showed that 56% of 5-benzylidene hydantoin was converted into phenylpyruvate. Further reflux (up to 90 minutes) did not increase the formation of phenylpyruvate.

EXAMPLE 7

In a 2-L three-necked, round-bottomed flask, fitted with a mechanical stirrer and a reflux condenser, were placed 120 g (1.2 moles) of hydantoin, 127 g (1.2 moles) of benzaldehyde and 9.0 g (0.12 mole) of 1-amino-2-propanol in 300 ml of water. The flask was then placed in an oil bath which had been heated to a temperature of 130°–135° C. After the mixture was refluxed for 4 hours, 600 g of 20% (3 moles) hot sodium hydroxide solution was added. The mixture was continued to reflux for 110 minutes. After cooling down to the room temperature, the solution was divided into six portions. Each portion contained 140 ml.

To each of the above six portions was added 0 g, 5.84 g (0.10 mole), 11.7 g (0.20 mole), 23.4 g (0.40 mole), 29.2 g (0.50 mole) and 35.1 g (0.60 mole) of sodium chloride respectively. After sodium chloride was completely dissolved, the solutions were acidified to pH 8.5 by adding concentrated hydrochloric acid (37%), and the resulting mixtures were then let to stand at room temperature overnight. The concentration of phenylpyruvate in the mother liquor for each mixture is shown in Table 1.

TABLE 1

| Sodium Chloride Added (mole) | Concentration of Phenylpyruvate (mM) |
| --- | --- |
| 0 | 88 |
| 0.10 | 56 |
| 0.20 | 40 |
| 0.40 | 31 |
| 0.50 | 16 |
| 0.60 | 13 |

EXAMPLE 8

In a 2-L three-necked, round-bottomed flask, fitted with a mechanical stirrer and a reflux condenser, were placed 120 g (1.2 moles) of hydantoin, 127 g (1.2 moles) of benzaldehyde and 9.0 g (0.12 mole) of 1-amino-2-propanol in 300 ml of water. The flask was then placed in an oil bath which had been heated to a temperature of 130°–135° C. After the mixture was refluxed for 4 hours, 720 g of 20% (3.6 moles) hot sodium hydroxide solution was added. The mixture was continued to reflux for 85 minutes. After cooling down to the room temperature, 140 g (2.4 moles) of sodium chloride was added.

The so obtained solution was transferred to a 3-L beaker, cooled in an ice bath, and brought to pH 8.5 by adding about 160 ml of concentrated hydrochloric acid (37%). The desired product, monohydrated sodium phenylpyruvate, precipitated slowly. The mixture was let to stand at room temperature for 16 hours.

The precipitate was filtered on a Büchner funnel, and then washed with 2.5 liters of methanol. After drying in a vacuum oven at 25° C. to a constant weight, 191 g (78% of the theoretical value) of monohydrated sodium phenylpyruvate was obtained.

EXAMPLE 9

The procedure of Example 8 was repeated except that diethanolamine (63 g, 0.60 mole) was used instead of 1-amino-2-propanol and that the time of reflux was 8 hours instead of 4 hours. The yield of monohydrated sodium phenylpyruvate was 122 g (50% of the theoretical value).

EXAMPLE 10

The procedure of Example 8 was repeated except that cyclohexylamine (23.8 g, 0.24 mole) was used instead of 1-amino-2-propanol and that the time of reflux was 14 hours instead of 4 hours. The yield of monohydrated sodium phenylpyruvate was 160 g (65% of the theoretical value).

EXAMPLE 11

In a 1-L three-necked, round-bottomed flask, fitted with a mechanical stirrer and a reflux condenser, were placed 30 g (0.30 mole) of hydantoin, 31.8 g (0.30 mole) of benzaldehyde and 2.25 g (0.030 mole) of 1-amino-2-propanol in 75 ml of water. The flask was then placed in an oil bath which had been heated to a temperature of 130°–135° C. After the mixture was refluxed for 4 hours, 180 g of 20% (0.90 mole) hot sodium hydroxide solution was added. The mixture was continued to reflux for 85 minutes. After cooling down to the room temperature, 35 g (0.60 mole) of sodium chloride was added.

The so obtained solution was divided into five portions. Each portion (57 ml) was transferred to a 100-ml beaker, and cooled in an ice bath. These five solutions were individually acidified to the pH values of 14, 8.5, 6.0, 4.5 and 3.0 by adding concentrated hydrochloric acid (37%). The mixtures were let to stand at room temperature for 16 hours.

Each precipitate was filtered on a Büchner funnel, washed with 60 ml of methanol, and transferred to a 100-ml beaker. It was then stirred with 48 ml of methanol, filtered again on a Büchner funnel, washed with two 45-ml portions of methanol, and dried in a vacuum oven at 25° C. The isolation yields of monohydrated sodium phenylpyruvate at various pHs are shown in Table 2.

TABLE 2

| pH | Yield of Monohydrated Sodium Phenylpyruvate | |
|---|---|---|
|  | g | % |
| 3.0 | 6.77 | 55 |
| 4.5 | 7.69 | 63 |
| 6.0 | 8.39 | 68 |
| 8.5 | 8.91 | 73 |
| 14 | 4.46 | 36 |

The above description is given on the preferred embodiments of the invention, but it will be apparent that many modifications and variations may be made by one skilled in the art without departing from the spirit or scope of the invention. Accordingly, the spirit or scope of the invention. Accordingly, the scope of the invention is defined in the following claims.

What is claimed is:

1. A process for the preparation of monohydrated sodium phenylpyruvate comprising the steps of:
   (a) reacting benzaldehyde with the stoichiometric quantity of hydantoin in an aqueous medium in the presence of a catalytic quantity of a primary or secondary amine having a boiling point greater than 100° C. at reflux temperature to form a reaction mixture;
   (b) treating the reaction mixture with 2 to 5 moles of sodium hydroxide per mole of hydantoin at reflux temperature to form a sodium hydroxide-treated solution;
   (c) adding sodium chloride to the sodium hydroxide-treated solution;
   (d) acidifying the solution obtained in step (c) to a pH range of 3.0 to 14 with concentrated hydrochloric acid; and
   (e) washing the precipitate formed in step (d) with a primary alcohol.

2. The process according to claim 1 wherein the primary amine is 1-amino-2-propanol or cyclohexylamine.

3. The process according to claim 1 wherein the secondary amine is diethanolamine.

4. The process according to claim 1 wherein sodium chloride is in an amount of 0.2 to 1.2 moles per mole of sodium hydroxide.

5. The process according to claim 1 wherein the solution obtained in step (c) is acidified to pH 8.5.

6. The process according to claim 1 wherein the primary alcohol is methanol.

* * * * *